(12) United States Patent
Martin et al.

(10) Patent No.: US 7,786,293 B2
(45) Date of Patent: *Aug. 31, 2010

(54) ORGANIC COMPOUNDS

(75) Inventors: Pierre Martin, Rheinfelden (CH);
Francois Jean Charles Natt, Aesch (CH)

(73) Assignee: Novartis AG, Basel (CH)

( * ) Notice: Subject to any disclaimer, the term of this patent is extended or adjusted under 35 U.S.C. 154(b) by 987 days.

This patent is subject to a terminal disclaimer.

(21) Appl. No.: 11/454,658

(22) Filed: Jun. 16, 2006

(65) Prior Publication Data

US 2006/0229445 A1    Oct. 12, 2006

Related U.S. Application Data

(63) Continuation of application No. 10/266,027, filed on Oct. 7, 2002, now Pat. No. 7,098,325, which is a continuation of application No. 09/416,031, filed on Oct. 12, 1999, now abandoned, which is a continuation of application No. 09/168,447, filed on Oct. 8, 1998, now abandoned.

(51) Int. Cl.
*C07H 21/00* (2006.01)
*C07D 417/00* (2006.01)
*C07D 285/08* (2006.01)

(52) U.S. Cl. .................. 536/25.3; 536/25.34; 548/123; 548/128

(58) Field of Classification Search ........................ None
See application file for complete search history.

(56) References Cited

U.S. PATENT DOCUMENTS 7,098,325 B2 *  8/2006  Martin et al. .............. 536/25.3

* cited by examiner

*Primary Examiner*—Traviss C McIntosh, III

(57) ABSTRACT

The present invention provides a process for the sulfurization of phosphorus-containing compounds. More particularly, the process involves contacting the compound to be sulfurized with a sulfur transfer reagent as defined hereinbefore in a solvent or a mixture of solvents.

12 Claims, No Drawings

ORGANIC COMPOUNDS

This application is a Continuation of application Ser. No. 10/266,027, filed on Oct. 7, 2002, now U.S. Pat. No. 7,098,325, which is a Continuation of application Ser. No. 09/416,031, filed on Oct. 12, 1999, now abandoned, which is a Continuation of application Ser. No. 09/168,447, filed Oct. 8, 1998, now abandoned. The contents of both are incorporated herein by reference in their entirety.

Phosphorothioate analogues of the phosphate moiety in compounds are of great interest in nucleic acid research, protein research, etc. For example, phosphorothioate-containing antisense oligonucleotides have been used in vitro and in vivo as inhibitors of gene expression.

Introduction of phosphorothioate moieties into oligonucleotides, assembled by solid-phase synthesis, can be achieved using either an H-phosphonate approach or a phosphoramidite approach. The H-phosphonate approach involves a single sulfur transfer step, carried out after the desired sequence has been assembled, to convert all of the internucleotide linkages to phosphorothioates. Alternatively, the phosphoramidite approach features a choice at each synthetic cycle: a standard oxidation provides the normal phosphodiester internucleotide linkage, whereas a sulfurization step introduces a phosphorothioate at the specific position in the sequence. An advantage of using phosphoroamidite chemistry, therefore, is the capability to control the state of each linkage in a site specific manner. The success of the phosphoramidite approach is dependent on the availability of efficient, good soluble sulfurization reagents that are compatible with automated DNA synthesis. A number of reagents have been designed and tested in recent years (WO 97/41130) but none of them is able to fulfill all the requirements for an ideal sulfurization reagent: excellent yields, good solubility, stable solutions, short reaction times, no formation of P=O units, no further reagents necessary, no side reactions with other parts of the molecule, odorless itself and odorless reaction products, capable of regeneration, and easily available.

The present invention provides a process for the sulfurization of phosphorus-containing compounds. This process involves contacting the compound to be sulfurized with a sulfur transfer reagent of formula (I)

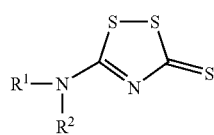

wherein $R^1$ is aryl which can be substituted by halo, $(C_1-C_6)$alkyl or $(C_1-C_6)$alkoxy, and $R^2$ is $(C_1-C_6)$ alkyl, which could also form a cyclic ring together with $R^1$.

Preferred are sulfur transfer reagents of formula (I) wherein $R^1$ is phenyl, tolyl, xylyl, naphthyl, 4-chlorophenyl or anisyl, and $R^2$ is methyl, ethyl, propyl or isopropyl Also preferred are sulfur transfer reagents of formula (II)

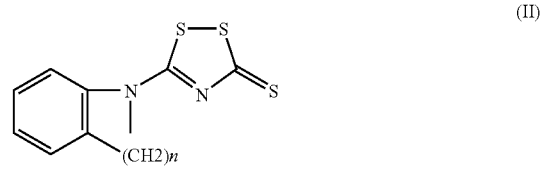

wherein n is 2 or 3.

The method of the present invention typically involves contacting a sulfur transfer reagent of formula (I) with a phosphorus-containing compound in solution or on a solid support, in a solvent or a mixture of solvents. The phosphorus in the phosphorus-containing compound is typically a trivalent phosphorus. Upon sulfurization, it becomes a pentavalent phosphorus. The trivalent phosphorus can be a phosphite, phosphonite, phosphonamidite, phosphine or any other phosphorus (III) derivative as part of the synthesis of DNA, RNA, phosphoropeptides, phosphonopeptides, phosphorylated nucleoside sugars or oligosaccharides.

Preferably the phosphorus containing compound is a compound of formula (III)

wherein each of $R^3$ and $R^4$ is a nucleoside or an oligonucleotide, and $R^5$ is a protective group. Preferably, $R^5$ is —$CH_2CH_2CN$, —$CH_2$—CH=CH—$CH_2CN$, —$CH_2CH_2$-4-nitrophenyl or —$CH_2CH$=$CH_2$.

For oligonucleotides, the sulfur transfer reagents of formula (I) or (II) do not modify the, nucleosidic residues, thereby preserving the genetic identity of the macromolecule. Thus the reagents of formula (I) or (II) and the process of the present invention can be reliably used in the automated synthesis of desired compounds. For example, the process is very useful for the automated synthesis up to gram scales of oligonucleotides, including both oligodeoxyribonucleotides and oligoribonucleotides of length from 4 to 50 bases containing the phosphorothioate substitution at either a single site or at all positions.

Typically, an amount of 1-30 molar equivalents, more preferably 2-10 molar equivalents, of the sulfur transfer reagent of formula (I) or (II) is used relative to the amount of the trivalent phosphorus groups in the phosphorus-containing compound. The reaction is typically carried out under an inert atmosphere, such as argon, although this is not required.

The sulfurization reaction occurs in a solvent. The solvent can be a hydrocarbon solvent, ethereal solvent, nitrile solvent, chlorinated solvent, heterocyclic solvent, etc. Specific examples of suitable solvents include pyridine, N,N-dimethylformamide (DMF), tetrahydrofuran (THF), acetonitrile and methylene chloride. Preferably, acetonitrile is used.

Although the reaction can be carried out at room temperature, it may also be carried out within a temperature range of about 0-50° C., and preferably 10-50° C. Typically, the conversion to the thioated compound is greater than 95%, mostly greater than about 99%.

A great advantage of the process of the present invention is that the compounds of formula (I) or (II) could be easily recovered from the reaction solution obtained from the automated synthesizer by reacting these solutions with sulfur or sulfur transfer reagents. In contrast, such recycling is not possible with the compounds described in WO 97/41130. Furthermore the sulfurization reaction described therein (see page 15 of WO 97/41130) leads to the formation of carbon-oxysulfide (COS) which is an easily flammable gas with a horrible odor. This formation of COS causes practical and safety problems.

The compounds of formula (I) and (II) could be prepared by the reaction of the corresponding thioureas with $CS_2$ and subsequent oxidation (DT 2404477 A1).

The following examples illustrate the invention but do not restrict it in any manner.

EXAMPLES

Preparation of the Thioureas

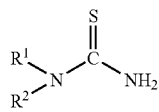

N-Ethylphenyl-thiourea ($R^1$=phenyl, $R^2$=ethyl)

A solution of 35.0 g (0.288 mol) of ethylaniline and 46.8 g (0.577 of mol) of NaSCN in 220 ml toluene is heated to 50° C. and a mixture of 31 ml trifluoroacetic acid and 45 ml toluene is added over a period of 3.5 h. The reaction mixture is then refluxed for 2.5 h. After cooling, the mixture is washed with water, dried and evaporated. The residue is treated with ether. After filtration, a beige powder is obtained, mp. 104 to 105° C.

The Following Analogues are Prepared:

| $R^1$ | $R^2$ | MP (° C.) | MS (M⁺) |
|---|---|---|---|
| 2,3-dimethylphenyl | ethyl | 93–94 | 208 |
| 4-methoxyphenyl | methyl | 126 | 196 |
| 1-naphthyl | ethyl | 124–125 | 230 |
| phenyl | methyl | 105–106 | 166 |
| 4-chlorophenyl | methyl | 125 | 200/202 |
| indoline | | 156 | 178 |
| tetrahydrochinoline | | 134–135 | 192 |

Preparation of Compounds of Formula (I)

Method A)

Preparation of N-ethyl,N-phenyl-5-amino-3H-1,2,4-dithiazol-3-thione ($R^1$=Phenyl, $R^2$=ethyl)

To a stirred mixture of 29.52 g (0.164 mmol) of N-ethyl-phenyl-thiourea, 14.9 g of $CS_2$ and 400 ml THF is added 8.17 g (0.34 mol) of NaH, in portions. After the production of hydrogen has ceased, the reaction mixture is heated for 2.5 h. After cooling, the precipitate is filtered, dissolved in 300 ml $H_2O$, and a solution of 41.56 g $I_2$ and 81.55 g KI in 500 ml $H_2O$ is added dropwise. The formed precipitate is filtered off and washed with hexane. Obtained are yellow crystals, mp 141° C.

Method B)

To a solution of 11.1 mmol of thiourea in 20 ml DMSO, 0.87 ml $CS_2$ and 1.56 g powdered KOH are added. After stirring for 24 h, the reaction mixture is poured into water and extracted with EtOAc. The extract is washed with water, dried ($Na_2SO_4$) and evaporated. The residue is chromatographed ($SiO_2$, hexane:EtOAc 6:1).

The Following Analogues (Method A or B) are Prepared:

| $R^1$ | $R^2$ | MS (M⁺) |
|---|---|---|
| 2,3-dimethylphenyl | ethyl | 282 |
| 4-methoxyphenyl | methyl | 270 |
| naphthyl | ethyl | 304 |
| phenyl | methyl | 240 |
| 4-chlorophenyl | methyl | 274/276 |
| indoline | | 252 |
| tetrahydrochinoline | | 266 |

Sulfurization Reaction

A) Reaction in Solution

To a solution of 0.786 mmol sulfurization reagent of formula (I) in 20 ml $CD_3CN$, 131 mg (0.786 mmol) of $P(OEt)_3$ are added. Immediately a sample of the reaction mixture is analyzed with $^{31}$P-NMR-spectrometry. Only one singulett at 68.587 ppm can be observed for $(EtO)_3P$=S, no signals at 18 ppm (mixed anhydride) and 0 ppm $(EtO)_3P$=O can be detected. The $^{13}$C-NMR-spectrum of a second sample shows no signals above 200 ppm, which means that no $CS_2$ is formed during the reaction.

B) Synthesis of Phosphorothioate Containing Oligonucleotides

For 1 □mole scale syntheses, a Perseptive Expedite MOSS synthesizer is used. The syntheses are performed on Polystyrene Primer support (Pharmacia) loaded with the 3' end residue. Solutions at 0.05M in acetonitrile of □-cyanoethyl deoxyribonucleosides phosphoramidites (Perseptive) or □-cyanoethyl 2'-methoxyethylribonucleosides phosphoramidites (P. Martin, Helvetica Chimica Acta, 78 (1995), 486-504) are used. In the coupling step, phosphoramidites are activated by benzimidazolium triflate (0.2M in acetonitrile; R. Noyori, J. Org. Chem. 61, 1996, 7996-7997). Non sulfurized phosphodiesters are oxidized by anhydrous t-butyl hydroperoxide (0.5M in toluene; this solution is obtained by diluting the toluene solution of t-butyl hydroperoxide from Lipomed). Capping and washing steps are carried out with standard reagents and solvents.

Typical cycles as well as the sulfurization conditions are shown in Table 1. The sulfur transfer reagent was used at a 0.1M concentration in acetonitrile. The volume of sulfurization reagent was 1.28 ml (including prime and purge volumes). Total contact time was 2 minutes.

Upon completion of solid-phase steps, the oligonucleotides (5' trityl-off) are cleaved from the support and deprotected with 30% ammonium hydroxide (2 h at room temperature for polypyrimidines and at 80° C. for mixed sequences), desalted on NAP-10 columns (Pharmacia) and analyzed by capillary gel electrophoresis and Maldi-Tof MS (see Table 2). Alternatively, the same process is applicable to trityl-on oligonucleotides suited for RP-HPLC purification.

TABLE 1

Synthetic conditions

| Step | Reagent/Solvent | Function | Time in sec. per cycle (repeat) |
|---|---|---|---|
| 1 | MeCN | Wash | 20 (2x) |
| 2 | 3% CCl$_3$COOH/CH$_2$Cl$_2$ | Detritylation | 20 + 40 |
| 3 | MeCN | Wash | 20 (2x) |
| 4 | Nucleotide/tetrazole/MeCN | Coupling | 180 |
| 5 | MeCN | Wash | 20 (2x) |
| 6 | PM-5468 0.1M in acetonitrile or 0.5M tBuOOH in DCM | Sulfurization/ Oxidation | 20 (2x) |
| 7 | MeCN | Wash | 20 (2x) |
| 8 | Ac$_2$O/lutidine/NMI/THF | Capping | 10 + 20 |
| 9 | MeCN | Wash | 20 (2x) |

TABLE 2 sequences and results (N: DNA; n: 2'-methoxyethyl RNA; s: phosphorothioate)

| Sequence | MW$_{calc.}$ | MW$_{meas.}$ |
|---|---|---|
| TsTT TTT TT | 2387.7 | 2387.7 |
| TTT TsTT TT | 2387.7 | 2386.5 |
| tstt ttt tt | 2980.4 | 2984.8 |
| ttt tstt tt | 2980.4 | 2985.6 |
| AsAsTs CsCsTs CsCsCs CsCsAs GsTsTs CsAsCs CsC | 6223.2 | 6222.8 |

C) Solid Phase Synthesis of a 20-mer Full Phosphorothiate Oligodeoxyribonucleotide Syntheses are performed on a Pharmacia OligoPilot II using 6.3 ml (150-200 □mole scale) or 24 ml (500 □mole scale) columns. Same reagents are used as in example B except for the support (Primer 30 HL loaded with the first 3' deoxyribonucleoside via a succinyl linker) and the phosphoramidites are dissolved as a 0.2M solution in acetonitrile.

Synthesis scale is based on weight and loading of the support. Excess and crude yields are calculated from the synthesis scale.

1.5 equivalent DNA phosphoramidite and the same excess of benzimidazolium triflate are simultaneously added to the column and recycled for 3 minutes. The synthetic conditions are shown in Table 3. The specific conditions for the sulfurization as well as the results are shown in Table 4. Crude material contained between 67 and 72% of full length material.

TABLE 3

Synthetic conditions on the OligoPilot II (Pharmacia)

| Step | Reagent/Solvent | Function | Volume or equiv. |
|---|---|---|---|
| 1 | MeCN | Wash | 6 CV |
| 2 | 3% CCl$_3$COOH/CH$_2$Cl$_2$ | Detritylation | 6 CV |
| 3 | MeCN | Wash | 6 CV |
| 4 | Nucleotide/tetrazole/MeCN | Coupling | 1.5 equiv |
| 5 | MeCN | Wash | 6 CV |
| 6 | STR | Sulfurization | See table 4 |
| 7 | MeCN | Wash | 6 CV |
| 8 | Ac$_2$O/lutidine/NMI/THF | Capping | 0.5 CV; 0.5 min. |
| 9 | MeCN | Wash | 6 CV |

TABLE 4 synthesis of the 20-mer phosphorothioate 5'-d(AATCCTCCCCCAGTTCACCC)

| STR | Solvent | Conc.(M) | Excess | Crude yield | P=O ($^{31}$P-NMR) |
|---|---|---|---|---|---|
| Van Boom | MeCN Picoline | 0.5 | 8 | 63.6% | <0.5% |
| Van Boom | MeCN Picoline | 0.5 | 4 | 60.4% | <0.5% |
| PM-5468 | MeCN | 0.1 | 8 | 66.5% | <0.5% |
| PM-5468 | MeCN | 0.1 | 4 | 68.8% | <0.5% |
| PM-5468 | THF | 0.2 | 4 | 68% | <0.5% |

Abbreviations:
STR: Sulfur Transfer reagent
PM-5468: Compound of formula (I) wherein R$^1$ is Phenyl and R$^2$ is Ethyl
Van Boom: Phenyl Acetyl Disulphide also named as PADS.
BT: Benzimidazolium Triflate Recyling of the reagent from the solutions obtained after the sulfurization step at the synthesizer Method A)

To the solutions collected after the sufurization step from the synthesizer, sulfur or sulfur dissolved in CS$_2$ is added. After 2 days, the solutions are filtered and evaporated. The residue is dissolved in EtOAc and filtered over a short SiO$_2$-column. After evaporation and washing of the residue with hexane, pure compounds of formula (I) are obtained.

Method B)

The solutions collected after the sufurization step from the synthesizer are evaporated. To the solution of the residue in acetone, sulfur is added, and the mixture is refluxed for 2 h and evaporated. The residue is treated with acetonitrile, filtered, evaporated and chromatographed. Pure compounds of formula (I) are obtained.

The invention claimed is:

1. A process for the sulfurization of a phosphorus-containing oligonucleotide which comprises contacting the phosphorus-containing oligonucleotide with a sulfur transfer reagent of formula (I)

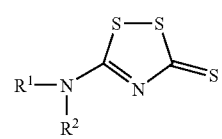

(I)

wherein
R$^1$ is aryl, which can optionally be substituted by halo, by (C$_1$-C$_6$) alkyl or by (C$_1$-C$_6$) alkoxy, and
R$^2$ is (C$_1$-C$_6$) alkyl, which can optionally form a cyclic ring together with R$^1$.

2. A process according to claim 1 wherein
R$^1$ is phenyl, tolyl, xylyl, naphthyl, 4-chlorophenyl or anisyl, and
R$^2$ is methyl, ethyl, propyl or isopropyl.

3. A process according to claim 1 wherein the sulfur transfer reagent is a compound of formula (II)

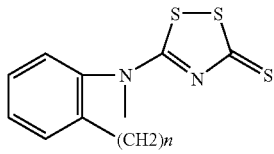
(II)

wherein n is 2 or 3.

4. A process according to claim 1 wherein the phosphorus-containing oligonucleotide is a trivalent phosphorus compound.

5. A process according to claim 4 wherein the trivalent phosphorus compound is a compound of formula (III)

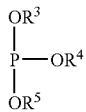
(III)

wherein each of $R^3$ and $R^4$ is a nucleoside or an oligonucleotide, and $R^5$ is a protective group.

6. A process according to claim 5 wherein $R^5$ is —CH$_2$CH$_2$CN, —CH$_2$—CH=CH—CH$_2$CN, —CH$_2$CH$_2$—4-nitrophenyl or —CH$_2$CH=CH$_2$.

7. A process according to claim 1 wherein the sulfur transfer reagent is used in an amount of 1-30 molar equivalents, relative to the amount of the phosphorus-containing oligonucleotide.

8. A process according to claim 1 wherein the reaction is carried out in the presence of a solvent selected from pyridine, DMF, THF, acetonitrile and methylene chloride.

9. A process according to claim 2 wherein the phosphorus-containing oligonucleotide is a trivalent phosphorus compound.

10. A process according to claim 3 wherein the phosphorus-containing oligonucleotide is a trivalent phosphorus compound.

11. A process according to claim 7 wherein the sulfur transfer reagent is used in an amount of 2-10 molar equivalents.

12. A process according to claim 8 wherein the solvent is acetonitrile.

* * * * *